United States Patent
Onuma et al.

(10) Patent No.: US 9,528,963 B2
(45) Date of Patent: Dec. 27, 2016

(54) BUFFER COMPOSITION

(71) Applicant: ARKRAY, Inc., Kyoto (JP)

(72) Inventors: Naotsugu Onuma, Kyoto (JP); Miho Fukuda, Kyoto (JP)

(73) Assignee: ARKRAY, Inc., Kyoto (JP)

(*) Notice: Subject to any disclaimer, the term of this patent is extended or adjusted under 35 U.S.C. 154(b) by 0 days.

(21) Appl. No.: 14/792,694

(22) Filed: Jul. 7, 2015

(65) Prior Publication Data

US 2016/0011150 A1    Jan. 14, 2016

(30) Foreign Application Priority Data

Jul. 9, 2014  (JP) .................. 2014-141829
Jul. 3, 2015  (JP) .................. 2015-134673

(51) Int. Cl.
*G01N 27/447*    (2006.01)
*B01L 3/00*    (2006.01)
*B01D 15/16*    (2006.01)

(52) U.S. Cl.
CPC ..... *G01N 27/44791* (2013.01); *B01L 3/50273* (2013.01); *G01N 27/44747* (2013.01); *B01D 15/166* (2013.01); *B01L 2400/0421* (2013.01); *Y10T 436/108331* (2015.01)

(58) Field of Classification Search
CPC ........... B01D 15/166; B01L 2400/0421; B01L 3/50273; G01N 27/447; G01N 27/44747; G01N 27/44791; G01N 33/48; Y10Y 436/10; Y10Y 436/108331; Y10Y 436/15; Y10Y 436/173845
USPC ....... 436/8, 18, 63, 100, 111, 149, 150, 161, 436/163; 252/408.1; 204/451
See application file for complete search history.

(56) References Cited

U.S. PATENT DOCUMENTS

| | | | |
|---|---|---|---|
| 4,139,440 A | 2/1979 | Chrambach et al. | |
| 5,246,558 A | 9/1993 | Chevigne et al. | |
| 5,510,245 A * | 4/1996 | Magers ................... | C12Q 1/32 435/14 |
| 2007/0278101 A1 | 12/2007 | Gomi et al. | |
| 2008/0171393 A1* | 7/2008 | Lu ............................ | A01N 1/02 436/18 |
| 2010/0044288 A1 | 2/2010 | Kitagawa | |
| 2011/0174621 A1* | 7/2011 | Yonehara ......... | G01N 27/44747 204/451 |

(Continued)

FOREIGN PATENT DOCUMENTS

EP    2144055 A1    1/2010
EP    2420844 A1    2/2012

(Continued)

OTHER PUBLICATIONS

Extended European Search Report issued in corresponding European Patent Application No. 15175632.7 dated Nov. 23, 2015.

(Continued)

*Primary Examiner* — Maureen Wallenhorst
(74) *Attorney, Agent, or Firm* — Morgan, Lewis & Bockius LLP

(57) ABSTRACT

Provided is a buffer composition capable of suppressing temperature dependency of the pH of a buffer solution, and a specimen analysis method and a specimen analysis system using the buffer composition, wherein the buffer composition contains a buffer substance A showing a positive correlation between temperature and pH and a buffer substance B showing a negative correlation between temperature and pH.

18 Claims, 2 Drawing Sheets

(56) References Cited

U.S. PATENT DOCUMENTS

| | | | |
|---|---|---|---|
| 2012/0322873 A1* | 12/2012 | Atkins | C02F 1/722 514/557 |
| 2012/0329040 A1* | 12/2012 | Herr | B01L 3/5023 435/5 |
| 2014/0030151 A1 | 1/2014 | Horii et al. | |

FOREIGN PATENT DOCUMENTS

| | | | |
|---|---|---|---|
| GB | 790557 | * | 2/1958 |
| JP | S53-013489 A | | 2/1978 |
| JP | H05-133938 A | | 5/1993 |
| JP | 11-287786 A | | 10/1999 |
| JP | 2005-528211 A | | 9/2005 |
| JP | 2007-322367 A | | 12/2007 |
| JP | 2010-048554 A | | 3/2010 |
| JP | 2012-215465 A | | 11/2012 |
| JP | 2013-007726 | | 1/2013 |
| WO | 03/103811 | | 12/2003 |
| WO | 2008/087218 A2 | | 7/2008 |
| WO | 2008/136321 A1 | | 11/2008 |

OTHER PUBLICATIONS

Canut et al., "Separation of plant membranes by electromigration techniques," Journal of Chromatography B, 722: 121-139 (1999).
Weber et al., "Counterbalancing hydrodynamic sample distortion effects increases resolution of free-flow zone electrophoresis," Electrophoresis, 19: 1104-1109 (1998).
Fukada et al., "Enthalpy and Heat Capacity Changes for the Proton Dissociation of Various Buffer Components in 0.1 M Potassium Chloride," Proteins: Structure, Function, and Genetics, 33: 159-166 (1998).
Office Action issued in corresponding Japanese Patent Application No. 2015-134673 dated Jun. 30, 2016.
Office Action issued in corresponding Japanese Patent Application No. 2015-134673 dated Nov. 8, 2016.

* cited by examiner

BUFFER COMPOSITION

BACKGROUND OF THE INVENTION

1. Field of the Invention

The present disclosure relates to a buffer composition, a specimen analysis method using the same, and a specimen analysis system using the same.

2. Description of Related Art pH buffer solutions (hereinafter, buffer solutions) are widely used in biology and chemistry for maintaining a constant pH in a solution. In general, a buffer solution is composed of an aqueous solution of a weak acid and its conjugate base, or a weak base and its conjugate acid. Depending on the acid dissociation constant (pKa) of the weak acid or the weak base, the pH range where the buffer solution exhibits its pH buffer capacity is determined. However, the pKa is known to change in a temperature-dependent manner, and as a result, a pH of the buffer solution also is subject to change in a temperature-dependent manner. The tendency and the level of the pH change vary depending on the particular weak acid or weak base in use.

Fukada recites influences of temperature with respect to pH of various buffer solutions ("PROTEINS: Structure, Function, Genetics" by Harumi Fukada et al., 1998, Vol. 33, pages 159-166). To avoid these influences on pH change due to temperature, in general, the pH is controlled at a solution temperature in use (or an assumed temperature). Further, JP H11(1999)-287786 A recites a method of intentionally utilizing a pH change in a buffer solution due to a change in temperature for analysis of an object.

A specimen analyzer or a specimen analysis system for analyzing components of specimens such as blood or urine is equipped with a temperature control function such as a temperature control unit, a thermostat, a temperature-controlling portion and the like so as to adjust the temperature of a specimen or a buffer solution used for a specimen analysis method for the purpose of improving the accuracy of analysis (see JP 2007-322367 A, JP 2010-48554 A, and JP2012-215465 A).

SUMMARY OF THE INVENTION

It has been found that in a case where the temperature control function is eliminated from a specimen analyzer or a specimen analysis system, a pH change of a buffer solution depending on temperature imposes a significant influence on the analytical result. Therefore, in one or more embodiments, it is an object of the present disclosure to provide a buffer composition capable of suppressing the temperature dependency of the pH of a buffer solution.

In one or more embodiments, the present disclosure relates to a buffer composition containing a buffer substance A showing a positive correlation between temperature and pH in a case of preparing the buffer solution at a predetermined pH, and a buffer substance B showing a negative correlation between temperature and pH in a case of preparing the buffer solution at a predetermined pH.

In another one or more embodiments, the present disclosure relates to a specimen analysis method or a specimen analysis system using the buffer composition according to the present disclosure.

In one or more embodiments, the present disclosure provides a buffer composition that can suppress the temperature dependency of the pH of a buffer solution. Furthermore, according to the present disclosure, in one or more embodiments, even when the accuracy of the temperature control is inferior, the pH change of the buffer solution can be decreased, and thus the accuracy of analysis of the specimen analysis method or the specimen analysis system can be improved. Further, according to the present disclosure, in one or more embodiments, it is possible to eliminate the temperature control function, and thus the specimen analysis method and specimen analysis system can be downsized and simplified. However, regardless of the temperature control accuracy, the buffer composition of the present disclosure can be used in any specimen analysis method, apparatus and system equipped with a temperature control function.

DETAILED DESCRIPTION OF THE INVENTION

Figure 1A:
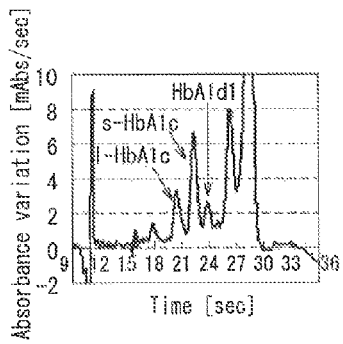
FIGS. 1A, 1B and 1C respectively show results under the respective environmental temperatures of 10° C., 25° C. and 35° C. in Example 5.

In one or more embodiments, the present disclosure is based on a finding that a temperature dependency of pH is suppressed in a buffer solution containing a buffer substance showing a positive correlation between temperature and pH, namely, a buffer substance where the pH of the buffer solution increases with a temperature increase, and a buffer substance showing a negative correlation between temperature and pH, namely, a buffer substance where the pH of the buffer solution decreases with a temperature increase. Further, in one or more embodiments, the present disclosure is based on a finding that a temperature control mechanism that has been provided to a conventional apparatus for analysis and measurement in the biological and chemical fields can be eliminated in the case of using a buffer solution with a suppressed temperature dependency of pH, and as a result, the apparatus can be downsized and simplified.

Namely in an aspect, the present disclosure relates to a buffer composition containing a buffer substance A showing a positive correlation between temperature and pH and a buffer substance B showing a negative correlation between temperature and pH (hereinafter, it is called also as "a buffer composition according to the present disclosure").

Although the details of the mechanism of suppressing the temperature dependency of the pH in the buffer composition according to the present disclosure have not been clarified, they can be assumed as follows. That is, since a buffer substance A showing a positive correlation between temperature and pH and a buffer substance B showing a negative correlation between temperature and pH are included, the temperature dependency of pH of the respective buffer substances cancel out each other, thereby suppressing the temperature dependency of pH. However, there is no necessity of interpreting the present disclosure limited by any mechanism.

Conventionally, it has been difficult to control a temperature-dependent pH change in a pH buffer solution. According to the present disclosure, in one or more embodiments, it is possible to suppress a pH change. Thereby, it is possible to keep the pH constant without controlling the temperature of the solution, and thus, it is possible to establish a measurement system that is free from the influence of the environmental temperature, without recourse to a temperature control mechanism of the apparatus. Furthermore, there is no necessity of providing a temperature control mechanism to the measurement apparatus, which results in downsizing and simplification of the apparatus. In one or more embodiments, the present disclosure contributes to downsizing and/or simplification of POCT (Point of Care Testing) apparatus.

[Buffer Substance A]

The buffer composition according to the present disclosure contains a buffer substance A showing a positive correlation between temperature and pH. An expression that a buffer substance "shows a positive correlation between temperature and pH" indicates that, when the buffer substance is in a state of solution, namely, in a state of buffer solution, the pH tends to increase with an increase in the temperature of the buffer solution. In one or more embodiments, the buffer substance A shows a positive correlation between temperature and pH around a pH where the pH buffer capability is exhibited. Further, other embodiments, a pH around the pKa of the buffer substance A or a pH within ±2 of the pKa of the buffer substance A, or a pH within ±1.5 of the pKa of the buffer substance A, or a pH within ±1 of the pKa of the buffer substance A shows a positive correlation. In addition, in other embodiments, the buffer substance A shows a positive correlation between temperature and pH at the pH of the buffer composition.

In one or more embodiments, the buffer substance A is a compound having a carboxy group or a salt thereof. In one or more embodiments, the valence of the carboxy group of the compound is monovalent or polyvalent, and examples of such polyvalence include bivalent, trivalent, tetravalent or more. In other embodiments, the buffer substance A is a compound having a carboxy group or a salt thereof, where the pKa of at least one carboxyl group is within ±2.0, ±1.5 or ±1.0 of the pH of the buffer composition.

In one or more embodiments, examples of the buffer substance A include: acids such as citric acid, maleic acid, acetic acid, malic acid, phthalic acid, oxalic acid, malonic acid, succinic acid, fumaric acid and the like, salts thereof; and a combination thereof. The buffer substance A in the buffer composition according to the present disclosure may be a single kind or may be two or more kinds.

[Buffer Substance B]

The buffer composition according to the present disclosure contains a buffer substance B showing a negative correlation between temperature and pH. An expression that a buffer substance "shows a negative correlation between temperature and pH" indicates that, when the buffer substance is in a state of solution, namely, in a state of buffer solution, the pH tends to lower with an increase in the temperature of the buffer solution. In one or more embodiments, the buffer substance B shows a negative correlation between temperature and pH at around a pH where the pH buffer capability is exhibited. Further, in other embodiments, a pH around the pKa of the buffer substance B or a pH within ±2 of the pKa of the buffer substance B, or a pH within ±1.5 of the pKa of the buffer substance B, or a pH within ±1 of the pKa of the buffer substance B shows a negative correlation. In addition, in other embodiments, the buffer substance B shows a negative correlation between temperature and pH at the pH of the buffer composition.

In one or more embodiments, examples of the buffer substance B include: an amine compound, phosphoric acid, boric acid, carbonic acid, phenol and a salt thereof; and a combination thereof. The buffer substance B in the buffer composition according to the present disclosure may be a single kind or may be two or more kinds. In a case where the amine compound has either an amino group or an imino group, in one or more embodiments, the valence is monovalence or polyvalence, and examples of the polyvalence include bivalence, trivalence, tetravalence or more. In another one or more embodiments, the buffer substance B is an amine compound or a salt thereof, where the pKa of at least one amino group or imino group is within ±2.0, ±1.5 or ±1.0 of the pH of the buffer composition.

In one or more non-limited embodiments, examples of the amine compound include a compound having an amino group ($-NH_2$), a compound having an imino group ($-NH-$), a compound having a nitrogen-containing heterocycle or the like.

In one or more embodiments, examples of the compound having an amino group ($-NH_2$) include N-(2-acetamide)-2-aminoethane sulfonic acid (ACES), N-(2-acetamide)iminodiacetic acid (ADA), tris(hydroxymethyl)aminomethane (Tris), and ethanolamine.

In one or more embodiments, examples of the compound having an imino group ($-NH_2$) include N-[tris(hydroxymethyl)methyl]-2-aminoethane sulfonic acid (TES), N-tris(hydroxymethyl)methyl-3-aminopropanesulfonic acid (TAPS), N-cyclohexyl-2-aminoethane sulfonic acid (CHES), N-cyclohexyl-3-aminopropanesulfonic acid (CAPS), and diethanolamine.

In one or more embodiments, a "nitrogen-containing heterocycle" in the present disclosure indicates a heterocycle having $-NH-$, $-NR-$ or $=N-$ in a ring. The heterocycle may be alicyclic or aromatic. Thus, in one or more embodiments, a compound having a nitrogen-containing heterocycle indicates a heterocyclic compound having $-NH-$, $-NR-$ (R is a group other than hydrogen) or $=N-$ in a ring, a compound having more than one of these groups, or a compound having the structure of the heterocyclic compound.

In one or more embodiments, examples of the compound having a nitrogen-containing heterocycle include piperazine, pyridine, imidazole, 2-morpholinoethanesulfonic acid (MES), 3-morpholinopropanesulfonic acid (MOPS), piperazine-N,N'-bis(2-ethanesulfonic acid)(PIPES), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), and 3-[4-(2-hydroxyethyl)-1-piperazinyl]propanesulfonic acid (EPPS).

Examples of other amine compounds include N,N-bis(2-hydroxyethyl)-2-aminoethane sulfonic acid (BES), triethanolamine, dimethylaminoethanol and the like.

[Compound Applicable as Buffer Substances A and B]

An amine compound having a carboxy group can serve as any one of the buffer substance A and the buffer substance B depending on the pH of the buffer composition. In one or more embodiments, "an amine compound having a carboxy group" in the present disclosure indicates a compound having a carboxy group together with an amino group ($-NH_2$), an imino group ($-NH-$) or a nitrogen-containing heterocycle in the same molecule. If the pH of the buffer composition according to the present disclosure is closer to the pKa of the carboxyl group rather than the pKa of the amino group, the imino group or the nitrogen-containing heterocycle of the compound, the compound can be used as a buffer substance A. If the pH of the buffer composition according to the present disclosure is closer to the pKa of the amino group, the imino group or the nitrogen-containing heterocycle rather than the pKa of the carboxy group of the compound, the compound can be used as a buffer substance B. In one or more embodiments, examples of the compound that can be used as the buffer substance A and the buffer substance B include N,N-bis(2-hydroxyethyl)glycine (Bicine), N-[tris(hydroxymethyl)methyl]glycine (Tricine), N-(2-acetamide)iminodiacetic acid (ADA), glutamine, glutamic acid, histidine, threonine, serine, arginine, glycine, alanine, β-alanine, α-aminobutyric acid, β-aminobutyric acid, valine, cysteine, methionine, asparagine, aspartic acid, proline, hydroxyproline, leucine, isoleucine, tyrosine, phenylalanine, ornithine, lysine, tryptophan and the like.

In one or more embodiments, regarding histidine, the pKa of the carboxy group is 1.82, the pKa of the side chain imidazoyl group is 6.00, and the pKa of the amino group of the α-carbon is 9.17. Therefore, for example, in a case where the pH of a buffer composition according to the present disclosure is 5.0, the closest pKa is of the amino group, and thus the histidine can be used as the buffer substance B. The other compounds applicable as the buffer substances A and B can be determined similarly to be either of the buffer substances A and B.

Therefore in one or more embodiments, the buffer substance A is a compound having a carboxy group and an amino group, an imino group or a nitrogen-containing heterocycle in the same molecule, and it is a compound used to make a buffer composition according to the present disclosure having a pH closer to the pKa of the carboxyl group rather than the pKa of the amino group, the imino group or the nitrogen-containing heterocycle. Further, in other embodiments, the buffer substance A is a compound where the pKa of at least one carboxyl group is within ±2.0, ±1.5 or ±1.0 of the pH of the buffer composition.

Similarly in one or more embodiments, the buffer substance B is a compound having a carboxy group and an amino group, an imino group or a nitrogen-containing heterocycle in the same molecule, and it is a compound used to make a buffer composition according to the present disclosure having a pH closer to the pKa of the amino group, the imino group or the nitrogen-containing heterocycle rather than the pKa of the carboxy group. Further, in other embodiments, the buffer substance B is a compound where the pKa of at least one amino group, imino group or nitrogen-containing heterocycle is within ±2.0, ±1.5 or ±1.0 of the pH of the buffer composition according to the present disclosure.

In one or more embodiments, the content of the buffer substances A and B in the buffer composition (in a liquid state) according to the present disclosure are respectively in a range of 0.5 mM to 500 mM, 1 mM to 300 mM, 5 mM to 200 mM, 10 mM to 100 mM, or, 20 mM to 50 mM.

[pKa]

In one or more embodiments, it is preferable that the buffer substance A and the buffer substance B have a pKa within ±2.0, ±1.5 or ±1.0 of the pH of the buffer composition according to the present disclosure, from the viewpoint of suppressing temperature dependency of pH. In the case of the buffer substance A, in one or more embodiments, the pKa is preferably the pKa of a carboxyl group. In the case of the buffer substance B, in one or more embodiments, the pKa is preferably the pKa of an amino group, an imino group or a nitrogen-containing heterocycle.

[pH]

The pH of the buffer composition (in a liquid state) according to the present disclosure can be selected suitably in accordance with the application of the buffer composition. In one or more embodiments, the pH of the buffer composition is in a range of 3.0 to 10.0, 3.5 to 9.0, 4.0 to 8.0, 4.5 to 7.5, or 4.5 to 6.5. The buffer composition may be in a liquid state, including water or a solution, or it may be in a dry state (e.g., a powder, freeze-dried, solid).

[Temperature]

In one or more embodiments, the temperature for using the buffer composition (in a liquid state) according to the present disclosure is preferably 0° C. or higher, higher than 0° C., 5° C. or higher, or 10° C. or higher, from the viewpoint of suppressing the temperature dependency of pH. In one or more embodiments, from the viewpoint of suppressing the temperature dependency of pH, the temperature is preferably 100° C. or lower, lower than 100° C., 60° C. or lower, or 50° C. or lower, from the viewpoint of suppressing the temperature dependency of pH. In one or more embodiments, the temperature is preferably 0° C. or higher and 100° C. or lower, higher than 0° C. and lower than 100° C., higher than 0° C. and not higher than 60° C., 5° C. or higher and not higher than 50° C., or 10° C. or higher and not higher than 50° C., from the viewpoint of suppressing the temperature dependency of pH. In one or more embodiments, the "temperature for using the buffer composition (in a liquid state)" according to the present disclosure indicates a temperature where the buffer composition in a liquid state can suppress the temperature dependency of pH.

[Other Components]

The buffer compositions according to the present disclosure may include other components as required. Examples of the other components include a component to be used for specimen analysis. In one or more embodiments, an example of the other component is a component used for capillary electrophoresis, and in one or more embodiments, the examples include a non-detergent amphoteric ionic substance, and/or, an ionic pseudostationary phase, and/or, a detergent, and/or, an antiseptic agent.

In one or more embodiments, from the viewpoint of improving the analytical accuracy, the non-detergent amphoteric ionic substance is preferably a non-detergent betaine, more preferably a non-detergent sulfobetaine and a non-detergent carboxy betaine, further preferably a non-detergent substance having a quaternary ammonium cation and a sulfo group ($-SO_3^-$) or a carboxy group ($-COO^-$) at sites not adjacent to each other in the same molecule, and even further preferably a non-detergent sulfobetaine (NDSB).

In one or more embodiments, the ionic pseudostationary phase is an ionic substance used in a capillary electrophoresis. Specifically it is an ionic substance used for separating substances in a specimen depending on the affinity (difference in distribution coefficient), thereby separating a substance as the analysis object in the specimen from other substances, i.e., for improving the separation accuracy. In one or more embodiments, an ionic pseudostationary phase that has been used or that may be used in the future can be selected in accordance with a specimen and/or a substance as an analysis object. In one or more embodiments, the ionic pseudostationary phase may be an anionic or cationic polymer. From the viewpoint of improving the analytical accuracy and shortening measurement time, the polymer may be a polysaccharide, and in one or more embodiments, the examples may include chondroitin sulfate, heparin, heparan, fucoidan, or the salts etc., and in particular, chondroitin sulfate or the salt is preferred. Examples of the chondroitin sulfate include chondroitin sulfate A, chondroitin sulfate C, chondroitin sulfate D, chondroitin sulfate E and the like.

[Preparation Method]

Although there is no particular limitation on the method for preparing a buffer composition according to the present disclosure, in one or more embodiments, the buffer composition can be prepared by mixing a buffer substance A, a buffer substance B and any other component as required or dissolving them in water. The buffer composition according to the present disclosure may be in a state of a buffer solution (solution capable of using the solution in the original state without dilution) or a concentrated liquid; or it may be a solid or a powder formed by freeze-drying or the like.

In one or more embodiments, the buffer composition according to the present disclosure is a buffer composition to be used for a specimen analysis method. In the present disclosure, in one or more embodiments, examples of the specimen analysis method include a specimen analysis method in which a reaction for specimen analysis is accompanied by an exothermic or endothermic reaction, i.e., a specimen analysis method that generates and/or absorbs heat. In one or more embodiments, an example thereof is a specimen separation analysis method. In one or more embodiments, the separation analysis method is a method of conducting an analysis while separating each analysis object included in the specimen, and the examples include high-performance liquid chromatography (HPLC), capillary electrophoresis (CE), or capillary electrochromatography. Examples of the high-performance liquid chromatography include cation exchange chromatography, anion cation exchange chromatography, partition chromatography, reversed phase partition chromatography, gel filtration chromatography, affinity chromatography and the like. Examples of capillary electrophoresis include capillary zone electrophoresis, capillary isotachophoresis, capillary isoelectric focusing electrophoresis, capillary electrokinetic chromatography, capillary gel electrophoresis, microchip electrophoresis and the like.

Therefore, in one or more embodiments, the buffer composition according to the present disclosure is a solution for capillary electrophoresis. In one or more non-limited embodiments, the "solution for capillary electrophoresis" in the present disclosure is a solution that can be used at least as a phoresis solution to fill the capillary channel before the capillary electrophoresis (hereinafter, this is called also as a "running buffer"), a phoresis solution to be used for phoresis in place of a sample after introduction of the sample into the capillary, a solution for preparing any of these phoresis solutions, or a solution for preparing a sample. A phoresis solution that can be used to fill the capillary channel before the capillary electrophoresis (running buffer) and the phoresis solution to be used for phoresis in place of a sample after introduction of the sample into the capillary may have the same or different makeup.

Furthermore, in one or more embodiments, the buffer composition according to the present disclosure is a solution for chromatography. In the present disclosure, in one or more non-limited embodiments, a "solution for chromatography" is a solution that can be used for at least any one of a mobile phase, a solution for preparing a mobile phase, or a solution for preparing a sample.

[Specimen Analysis Method]

In one aspect, the present disclosure relates to a specimen analysis method that uses a buffer composition according to the present disclosure. In one or more embodiments, the specimen analysis method according to the present disclosure is a method with a lower accuracy in temperature control, and in one or more embodiments, it is a method of not using a temperature controller. In one or more embodiments, the specimen analysis method is for example the above mentioned specimen separation analysis method, and in one or more embodiments, the examples include HPLC, CE, capillary electrochromatography and the like.

In one or more embodiments, examples of specimen for the specimen analysis method in the present disclosure include biological samples of human beings or animals other than human beings, more specifically, urine, blood, a sample derived from blood, body fluids and the like. Examples of a measurement object in the specimen analysis method includes components in the above-mentioned specimens, and examples of a component as a measurement objects in blood or in a sample derived from blood include hemoglobin, glycosylated hemoglobin, albumin and the like.

[Specimen Analysis System]

In another aspect, the present disclosure relates to a specimen analysis system using a buffer composition according to the present disclosure. In one or more embodiments, the specimen analysis system according to the present disclosure is a system for conducting a specimen analysis method according to the present disclosure, and, in one or more embodiments, a system with a lower accuracy in temperature control, or, in one or more embodiments, a system not having a temperature controller.

In one or more embodiments, the specimen analysis system can include an analysis chip (analysis cartridge), an analysis stationary phase (carrier) and the like to be used for a specimen analysis. The analysis chip is provided with, for example, a capillary, a microchannel, a reaction portion to react with a measurement object, and/or, a detection portion to detect a measurement object. In another one or more embodiments, the specimen analysis system can include one or a combination of two or more of a mechanism for detecting a measurement object (detection portion, detector), a mechanism for running a phoresis solution or a phoresis phase (liquid-sending portion, liquid sender, voltage application portion, voltage applicator), a mechanism for recording a detection result (memory, memory storage), and/or, a mechanism for displaying the detection result (display portion, display apparatus).

In one or more embodiments, examples of the specimen analysis method and specimen analysis system according to the present disclosure include a HPLC system, a CE system, or a capillary electrochromatography system using the buffer composition.

[Kit]

In another aspect, the present disclosure relates to a kit including a combination of the buffer substance A and the buffer substance B. The kit according to the present disclosure can include further the above-mentioned analysis chip or analysis stationary phase. The kit according to the present disclosure can be used for preparation of the buffer composition according to the present disclosure, and it can be used in the specimen analysis method and the specimen analysis system according to the present disclosure.

The present invention can relate to the following one or more embodiments.

[A1] A buffer composition comprising a buffer substance A showing a positive correlation between temperature and pH and a buffer substance B showing a negative correlation between temperature and pH.

[A2] The buffer composition according to [A1], wherein the buffer substance A is a compound having a carboxy group or a salt thereof.

[A3] The buffer composition according to [A1] or [A2], wherein the buffer substance B is selected from the group consisting of: an amine compound, phosphoric acid, boric acid, carbonic acid, phenol, and a salt thereof; and a combination thereof.

[A4] The buffer composition according to any one of [A1] to [A3], wherein the pKa of the buffer substance A and the pKa of the buffer substance B are respectively within ±2.0, ±1.5 or ±1.0 of the pH of the buffer composition in a liquid state.

[A5] The buffer composition according to any one of [A1] to [A4], wherein the buffer composition is a liquid having a pH in a range of 3.0 to 10.0, 3.5 to 9.0, 4.0 to 8.0, 4.5 to 7.5, or 4.5 to 6.5.

[A6] The buffer composition according to any one of [A1] to [A5], which is used for a specimen analysis method.

[A7] The buffer composition according to [A6], wherein the specimen analysis method is a specimen analysis method that generates and/or absorbs heat.

[A8] The buffer composition according to any one of [A1] to [A7], which is used for a high-performance liquid chromatography (HPLC), a capillary electrophoresis (CE), or a capillary electrochromatography.

[A9] The buffer composition according to any one of [A1] to [A8], further containing an ionic pseudostationary phase.

[A10] The buffer composition according to any one of [A1] to [A9], further containing a non-detergent amphoteric ionic substance.

[A11] A specimen analysis method, using the buffer composition according to any one of [A1] to [A10].

[A12] A specimen analysis system, using the buffer composition according to any one of [A1] to [A10].

[A13] The specimen analysis system according to [A12], not having a temperature controller.

[A14] A specimen analysis kit having the buffer composition used for a specimen analysis method according to any one of [A1] to [A10], and optionally, a specimen analysis chip used for a specimen analysis method.

EXAMPLES

The present disclosure will be described below more specifically by referring to the following Examples, though the Examples are not intended to limit the present disclosure.

Example 1

Comparative Examples 1, 2

Buffer solutions of Example 1 (pH 7.0) and Comparative Examples 1, 2 were prepared in the following manner by using maleic acid (pKa=1.94, 6.54) and PIPES (piperazine-1,4-bis(2-ethanesulfonic acid) (pKa=6.76) as the buffer substances. These buffer solutions were heated or cooled, and the pH was measured with a pH meter at a temperature in a range of 10° C. to 50° C. Here, the pH indicates a numerical value taken 2 minutes after immersing an electrode of the pH meter (manufactured by Horiba, Ltd.) in the measurement object (the same is true in the following). ΔpH, which is the difference between the highest value and the lowest value of the measured pH, and ΔpH/° C. (SLOPE function), which is the slope of a regression line of pH change in accordance with temperature, were calculated. The results are illustrated in Table 1 below.

Buffer Solution of Example 1

20 mM maleic acid, 20 mM PIPES (pH 7.0, 24° C., controlled with NaOH)

Buffer Solution of Comparative Example 1

40 mM maleic acid (pH 7.0, 24° C., controlled with NaOH)

Buffer Solution of Comparative Example 2

40 mM PIPES (pH 7.0, 24° C., controlled with NaOH)

TABLE 1

| Temperature (° C.) | Example 1 pH measured value | Comparative Example 1 pH measured value | Comparative Example 2 pH measured value |
|---|---|---|---|
| 10 | 6.956 | 6.890 | 7.200 |
| 15 | 6.971 | 6.954 | 7.148 |
| 20 | 6.978 | 6.983 | 7.119 |
| 25 | 6.980 | 6.984 | 7.074 |
| 30 | 6.984 | 6.985 | 7.041 |
| 35 | 6.982 | 6.991 | 6.990 |
| 40 | 6.980 | 7.002 | 6.945 |
| 45 | 6.989 | 7.014 | 6.921 |
| 50 | 7.039 | 7.023 | 6.879 |
| ΔpH | 0.083 | 0.133 | 0.321 |
| ΔpH/° C. | 0.0013 | 0.0025 | −0.0080 |

As illustrated in Table 1, the buffer solution of Example 1 had a smaller temperature-dependent change of pH in comparison with the buffer solutions of Comparative Examples 1 and 2.

Example 2

Comparative Examples 3, 4

Buffer solutions of Example 2 and Comparative Examples 3, 4 were prepared (pH 5.0) in the following manner by using glutamic acid (pKa=2.19, 4.25, 9.67) and piperazine (pKa=5.68, 9.82) as the buffer substances. Regarding these buffer solutions, ΔpH and ΔpH/° C. were calculated similarly to Example 1. The results are illustrated in Table 2 below.

Buffer Solution of Example 2

35 mM glutamic acid, 5 mM piperazine (pH 5.0, 24° C., controlled with NaOH)

Buffer Solution of Comparative Example 3

40 mM glutamic acid (pH 5.0, 24° C., controlled with NaOH)

Buffer Solution of Comparative Example 4

40 mM piperazine (pH 5.0, 24° C., controlled with HCl)

For each of these buffer solutions, pH was measured similarly to the above-mentioned Example 1.

TABLE 2

| Temperature (° C.) | Example 2 pH measured value | Comparative Example 3 pH measured value | Comparative Example 4 pH measured value |
| --- | --- | --- | --- |
| 5 | 5.034 | 5.005 | 5.341 |
| 10 | 5.033 | 5.016 | 5.276 |
| 15 | 5.027 | 5.034 | 5.243 |
| 20 | 5.034 | 5.047 | 5.167 |
| 25 | 5.035 | 5.054 | 5.093 |
| 30 | 5.035 | 5.061 | 5.002 |
| 35 | 5.001 | 5.066 | 4.851 |
| 40 | 4.996 | 5.060 | 4.781 |
| 45 | 4.994 | 5.076 | 4.683 |
| 50 | 4.985 | 5.087 | 4.608 |
| ΔpH | 0.050 | 0.071 | 0.733 |
| ΔpH/° C. | −0.0012 | 0.0015 | −0.0171 |

As illustrated in Table 2, the buffer solution of Example 2 had a smaller temperature-dependent change of pH in comparison with the buffer solutions of Comparative Examples 3 and 4.

Example 3

Comparative Examples 5, 6

Buffer solutions of Examples 3, 4 and Comparative Examples 5, 6 were prepared (pH 5.0) in the following manner by using citric acid (pKa=3.09, 4.75, 6.41) and histidine (pKa=1.82, 6.00, 9.17) or piperazine (pKa=5.68, 9.82) as the buffer substances, and furthermore using sodium chondroitin sulfate C as a substance other than the buffer substances. Regarding these buffer solutions, ΔpH and ΔpH/° C. were calculated similarly to Example 1. The results are illustrated in Table 3 below.

Buffer Solution of Example 3

40 mM citric acid, 40 mM histidine, 1.25% w/v sodium chondroitin sulfate C (pH 5.0, 24° C., controlled with NaOH)

Buffer Solution of Example 4

40 mM citric acid, 20 mM piperazine, 1.25% w/v sodium chondroitin sulfate C (pH 5.0, 24° C., controlled with NaOH)

Buffer Solution of Comparative Example 5

40 mM citric acid, 1.25% w/v sodium chondroitin sulfate C (pH 5.0, 24° C., controlled with NaOH)

Buffer Solution of Comparative Example 6

40 mM histidine (pH 5.0, 24° C., controlled with NaOH)

TABLE 3

| Temperature (° C.) | Example 3 pH measured value | Example 4 pH measured value | Comparative Example 5 pH measured value | Comparative Example 6 pH measured value |
| --- | --- | --- | --- | --- |
| 10 | 4.970 | 4.963 | 4.827 | 4.992 |
| 15 | 4.995 | 4.983 | 4.843 | 4.975 |
| 20 | 5.008 | 4.990 | 4.888 | 4.950 |
| 25 | 4.995 | 4.991 | 4.920 | 4.930 |
| 30 | 5.020 | 4.992 | 4.949 | 4.919 |
| 35 | 4.996 | 5.013 | 5.006 | 4.904 |
| 40 | 4.998 | 5.045 | 5.072 | 4.875 |
| 45 | 4.972 | 5.050 | 5.120 | 4.845 |
| 50 | 4.965 | 5.051 | 5.153 | 4.816 |
| ΔpH | 0.055 | 0.088 | 0.326 | 0.176 |
| ΔpH/° C. | −0.0004 | 0.0023 | 0.0086 | −0.0042 |

As illustrated in Table 3, the buffer solutions of Examples 3 and 4 had smaller temperature-dependent changes of pH in comparison with the buffer solutions of Comparative Examples 5 and 6.

Example 5

Blood was used for the specimen so as to perform a specimen analysis for hemoglobin in the blood by using a capillary electrophoresis chip.

Capillary Electrophoresis Chip

Figure 4:
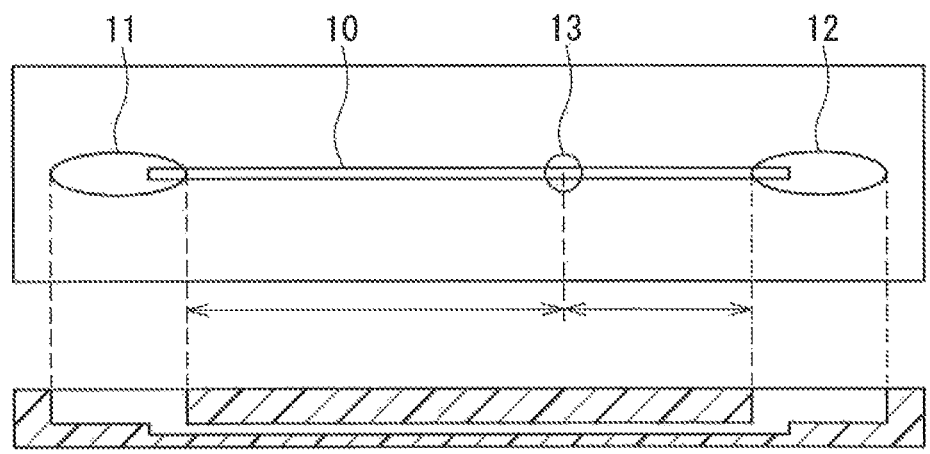
FIG. 4 is a schematic view of one example of a chip for a capillary electrophoresis.

For the capillary electrophoresis chip, a chip shown in the schematic view of FIG. 4 was used. The chip has a microchannel 10 inside, and a sample reservoir 11 and an electrophoresis solution reservoir 12 are formed at the respective ends of the microchannel 10. A detection portion 13 is formed on the upper face of the microchannel 10 between the sample reservoir 11 and the electrophoresis solution reservoir 12. For the material of the chip, PMMA (polymethylmethacrylate) was used. The channel 10 was set to be 0.04 mm×0.04 mm×30 mm, and the capacities of the sample reservoir 11 and the electrophoresis solution reservoir 12 were set to 10 μL. The detection portion 13 was located such that the center would be distanced by respectively 20 mm and 10 mm from the sample reservoir 11 and the electrophoresis solution reservoir 12.

<Electrophoresis Solution>
(Electrophoresis Solution 1)
40 mM citric acid
1% w/v sodium chondroitin sulfate C
500 mM NDSB-201 (non-detergent sulfobetaine, manufactured by Tokyo Chemical Industry Co., Ltd.)
0.1% w/v Emulgen LS-110 (manufactured by Kao Corporation)
0.02% sodium azide
Dimethylaminoethanol (for pH control)
pH 6.0
(Electrophoresis Solution 2)
40 mM citric acid
20 mM histidine
1.25% w/v sodium chondroitin sulfate C
0.1% w/v Emulgen LS-110 (manufactured by Kao Corporation)
0.02% sodium azide
Dimethylaminoethanol (for pH control)
pH 5.0
<Capillary Electrophoresis>
The capillary electrophoresis was conducted in the following manner. For the measurement, a dedicated device manufactured by Arkray, Inc. was used. Temperature control for the respective solutions and the microchannel chip was not conducted.

1. A capillary electrophoresis chip was set in the electrophoresis apparatus manufactured by Arkray, Inc.
2. The electrophoresis solution 2 (9 µL) was introduced into the electrophoresis solution reservoir of the chip, and the microchannel was filled with the electrophoresis solution 2 by use of the capillary phenomenon.
3. Human whole blood was diluted 41 times with the electrophoresis solution 1, thereby making a sample.
4. The sample (9 µL) was introduced into the electrophoresis solution reservoir of the chip.
5. A positive electrode was brought into contact with the sample reservoir, and a negative electrode was brought into contact with the electrophoresis solution reservoir, thereby starting an electrophoresis under a constant current control.
6. Absorbance at 415 nm was measured at the detection portion so as to obtain an electropherogram. The electrophoresis was conducted for 60 seconds.

Figure 1B:
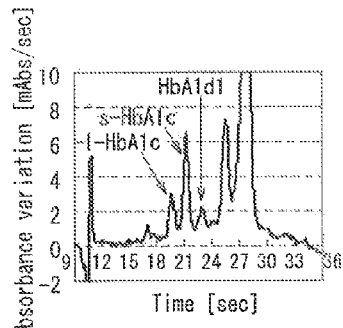
Figure 1C:
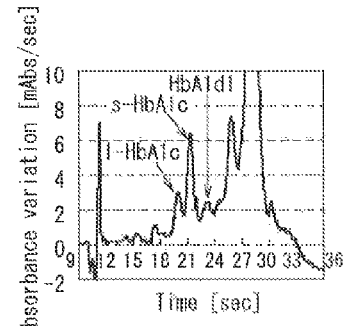

This measurement was performed under respective environmental temperatures of 10° C., 25° C. and 35° C. The results are illustrated in FIGS. 1A-1C. FIGS. 1A, 1B, and 1C illustrate respectively the results under respective environmental temperatures of 10° C., 25° C. and 35° C. in Example 5.

Example 6

Measurement was conducted similarly to Example 5 except that the electrophoresis solution 2 in the above Example 5 was replaced by an electrophoresis solution 3 as described below.
(Electrophoresis Solution 3)
40 mM citric acid
20 mM piperazine
1.25% w/v sodium chondroitin sulfate C
0.1% w/v Emulgen LS-110 (manufactured by Kao Corporation)
0.02% sodium azide
Dimethylaminoethanol (for pH control)
pH 5.0

Figure 2A:
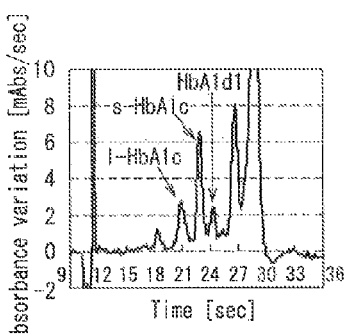
FIGS. 2A, 2B and 2C respectively show results under the respective environmental temperatures of 10° C., 25° C. and 35° C. in Example 6.
Figure 2B:
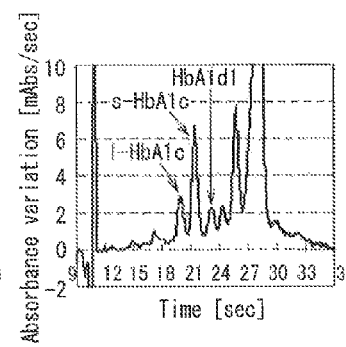
Figure 2C:
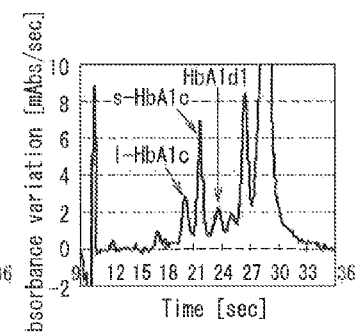

The results are illustrated in FIGS. 2A-2C. FIGS. 2A, 2B, and 2C illustrate respectively the results under respective environmental temperatures of 10° C., 25° C. and 35° C. in Example 6.

Comparative Example 7

Measurement was conducted similarly to Example 5 except that the electrophoresis solution 2 in the above Example 5 was replaced by an electrophoresis solution 4 as described below.
(Electrophoresis Solution 4)
40 mM citric acid
1.25% w/v sodium chondroitin sulfate C
0.1% w/v Emulgen LS-110 (manufactured by Kao Corporation)
0.02% sodium azide
Dimethylaminoethanol (for pH control)
pH 5.0

Figure 3A:
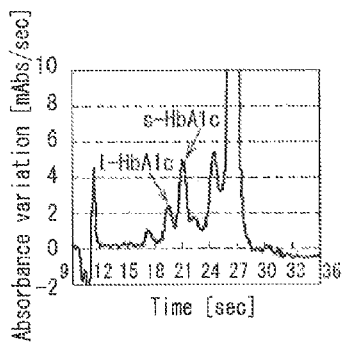
FIGS. 3A, 3B and 3C respectively show results under the respective environmental temperatures of 10° C., 25° C. and 35° C. in Comparative Example 7.
Figure 3B:
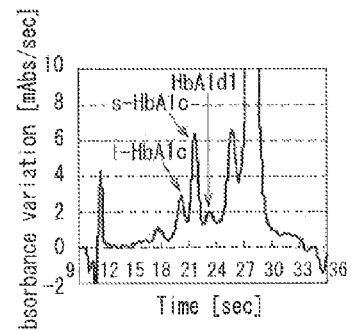
Figure 3C:
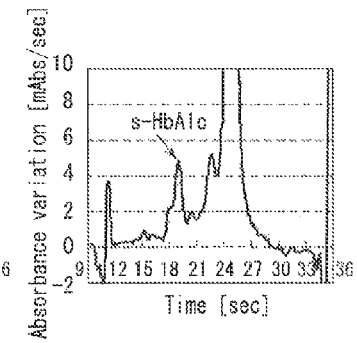

The results are illustrated in FIGS. 3A-3C. FIGS. 3A, 3B, and 3C illustrate respectively the results under respective environmental temperatures of 10° C., 25° C. and 35° C. in Comparative Example 7.

In the analyses of Examples 5 and 6, as illustrated in FIGS. 1A-1C and 2A-2C, separation of l-HbA1c, s-HbA1c and HbA1d1 can be confirmed at all of the temperatures. This shows that the influence of the environmental temperature was low In contrast, in Comparative Example 7, as illustrated in FIGS. 3A-3C, separation of l-HbA1c, s-HbA1c and HbA1d1 was confirmed at 25° C., but separation of HbA1d was not confirmed at 10° C., and at 35° C., separation was confirmed only for s-HbA1c. This shows that the influence of the environmental temperature was high.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method of analyzing a specimen in a sample comprising subjecting the sample to high-performance liquid chromatography (HPLC), capillary electrophoresis (CE), or capillary electrochromatography using a buffer composition,
wherein the buffer composition comprises:
 a buffer substance A showing a positive correlation between temperature and pH;
 a buffer substance B showing a negative correlation between temperature and pH;
 a non-detergent amphoteric ionic substance; and
 an ionic pseudostationary phase,
wherein:
 the buffer composition is a liquid having a pH in a range of 3.0 to 10.0,
 the pKa of the buffer substance A and the pKa of the buffer substance B are each within ±2.0 of the pH of the buffer composition,
 the buffer substance A is selected from the group consisting of citric acid, maleic acid, acetic acid, glutamic acid, malic acid, phthalic acid, oxalic acid, malonic acid, succinic acid, fumaric acid, and a salt thereof; an anime compound having a carboxy group; and a combination thereof,
 the buffer substance B is selected from the group consisting of an amine compound, phosphoric acid, boric acid, carbonic acid, phenol, and a salt thereof; an anime compound having a carboxy group; and a combination thereof and,
 the ionic pseudostationary phase is selected from the group consisting of chondroitin sulfate, heparin, fucoidan, and a salt thereof, and a combination thereof.

2. A specimen analysis system comprising the buffer composition as defined in claim 1.

3. The specimen analysis system according to claim 2, wherein a temperature controller is not present.

4. The method according to claim 1, wherein the non-detergent amphoteric ionic substance is selected from the group consisting of a non-detergent sulfobetaine, a non-detergent carboxy betaine, and a combination thereof.

5. The method according to claim 1, wherein the non-detergent amphoteric ionic substance is a non-detergent sulfobetaine.

6. The method according to claim 1, wherein the buffer substance A is selected from the group consisting of citric acid, maleic acid, malic acid, phthalic acid, oxalic acid, malonic acid, succinic acid, fumaric acid, and a salt thereof; glutamic acid; and a combination thereof.

7. The method according to claim 1, wherein the buffer substance A is selected from the group consisting of citric acid, maleic acid, and a salt thereof; glutamic acid; and a combination thereof.

8. The method according to claim 1, wherein the buffer substance B is the amine compound or the amine compound having a carboxy group.

9. The method according to claim 8 wherein the amine compound is selected from the group of piperazine, pyridine, imidazole, 2-morpholinoethanesulfonic acid (MES), 3-morpholinopropanesulfonic acid (MOPS), piperazine-N,N'-bis(2-ethanesulfonic acid)(PIPES), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), and 3-[4-(2-hydroxyethyl)-1-piperazinyl]propanesulfonic acid (EPPS).

10. The method according to claim 8, wherein the amine compound having a carboxy group is selected from the group of N,N-bis(2-hydroxyethyl)glycine (Bicine), N-[tris(hydroxymethyl)methyl]glycine (Tricine), N-(2-acetamide)iminodiacetic acid (ADA), glutamine, glutamic acid, histidine, threonine, serine, arginine, glycine, alanine, β-alanine, α-aminobutyric acid, β-aminobutyric acid, valine, cysteine, methionine, asparagine, aspartic acid, proline, hydroxyproline, leucine, isoleucine, tyrosine, phenylalanine, ornithine, lysine, and tryptophan.

11. The method according to claim 1, wherein the buffer substance B is selected from the group consisting of PIPES (piperazine-1,4-bis(2-ethanesulfonic acid), piperazine, histidine, and a combination thereof.

12. The method according to claim 1, wherein the buffer composition comprises any one of the following combinations: maleic acid and PIPES (piperazine-1,4-bis(2-ethanesulfonic acid); glutamic acid and piperazine; citric acid and histidine; and citric acid and piperazine.

13. The method according to claim 1, wherein the pKa of the buffer substance A and the pKa of the buffer substance B are within ±1.5 of the pH of the buffer composition.

14. The method according to claim 1, wherein the pKa of the buffer substance A and the pKa of the buffer substance B are within ±1.0 of a pH of the buffer composition.

15. The method according to claim 1, wherein the buffer composition has a pH in a range of 4.0 to 8.0.

16. The method according to claim 1 further comprising introducing the buffer composition into a capillary channel.

17. The method according to claim 1, wherein the method does not use a temperature controller.

18. The method according to claim 1 further comprising preparing the sample with the buffer composition.

* * * * *